United States Patent
Cheng et al.

(10) Patent No.: US 10,336,751 B2
(45) Date of Patent: Jul. 2, 2019

(54) TRICYCLIC 4-PYRIDONE-3-CARBOXYLIC ACID DERIVATIVES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Xingchun Han, Shanghai (CN); Chungen Liang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 101 days.

(21) Appl. No.: 15/866,954

(22) Filed: Jan. 10, 2018

(65) Prior Publication Data

US 2018/0134705 A1 May 17, 2018

Related U.S. Application Data

(63) Continuation of application No. PCT/EP2016/067002, filed on Jul. 18, 2016.

(51) Int. Cl.
*C07D 471/04* (2006.01)
*A61P 31/20* (2006.01)

(52) U.S. Cl.
CPC .......... *C07D 471/04* (2013.01); *A61P 31/20* (2018.01)

(58) Field of Classification Search
CPC .................................................... C07D 471/04
USPC .............................. 540/585; 514/214, 214.01
See application file for complete search history.

(56) References Cited

FOREIGN PATENT DOCUMENTS

| CA | 2093107 | 3/1993 |
|---|---|---|
| JP | S60197684 A | 7/1985 |
| WO | 2015/173614 A1 | 11/2015 |
| WO | 2016/071215 A1 | 5/2016 |
| WO | 2015-113990 A1 | 8/2016 |
| WO | 2016/128335 A1 | 8/2016 |

OTHER PUBLICATIONS

Georgopapadakou et al., "Monocyclic and Tricyclic Analogs of Quinolones: Mechanism of Action" Antimicrobial Agents and Chemotherapy, 31(4):614-616 ( 1987).
Buzhe Xu et al., "A facile synthesis of novel tricyclic 4-pyridones" Tetrahedron Letters 55(52):7194-7197 ( 2014).
Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48(4):1229-1236 ( 2005).
Geng et al., "Small-molecule inhibitors for the treatment of hepatitis B virus documented in patents" Mini Reviews in Medicinal Chemistry 13(5):749-776 (Apr. 1, 2013).
ISR for PCT/EP2016/067002 (dated Aug. 18, 2016).

*Primary Examiner* — Patricia L Morris
(74) *Attorney, Agent, or Firm* — Brian L. Buckwalter

(57) ABSTRACT

The invention provides novel compounds having the general formula:

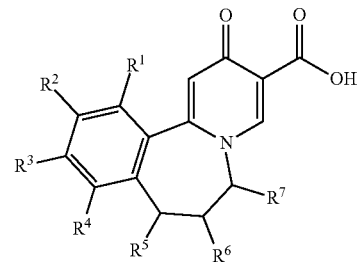

wherein $R^1$ to $R^7$ are as described herein, compositions including the compounds and methods of using the compounds.

12 Claims, No Drawings

TRICYCLIC 4-PYRIDONE-3-CARBOXYLIC ACID DERIVATIVES FOR THE TREATMENT AND PROPHYLAXIS OF HEPATITIS B VIRUS INFECTION

CROSS REFERENCE TO RELATED APPLICATIONS

This application is a continuation of International Application No. PCT/EP2016/067002 having an international filing date of Jul. 18, 2016 and which claims benefit under 35 U.S.C. § 119 to International Application No. PCT/CN2015/084601 having an international filing dated of Jul. 21, 2015. The entire contents of both are incorporated herein by reference.

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel tricyclic 4-pyridone-3-carboxylic acid derivatives having pharmaceutical activity, their manufacture, pharmaceutical compositions containing them and their potential use as medicaments.

The present invention relates to compounds of formula I

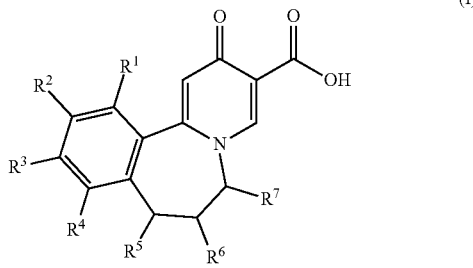

(I)

wherein $R^1$ to $R^7$ are as described below, or pharmaceutically acceptable salts, or enantiomers, or diastereomer thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impp/Impa nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295). HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

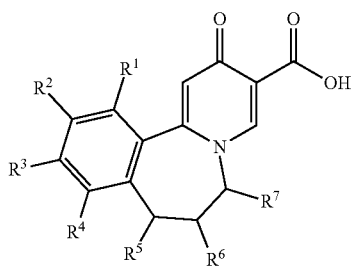

(I)

wherein
$R^1$, $R^2$, $R^3$ and $R^4$ are independently selected from $C_{1-6}$alkyl, halo$C_{1-6}$alkyl, hydrogen, halogen, amino, cyano, pyrrolidinyl and $OR^8$;
$R^5$, $R^6$, $R^7$ are independently selected from hydrogen, $C_{1-6}$alkyl or halo$C_{1-6}$alkyl;
$R^8$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$alkyl; $C_{1-6}$alkoxy-$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkyl-carbonylamino$C_{1-6}$alkyl; $C_{1-6}$alkylsulfonylamino$C_{1-6}$alkyl; $C_{1-6}$alkoxycarbonylamino$C_{1-6}$alkyl; pyrazolyl$C_{1-6}$alkyl; triazolyl$C_{1-6}$alkyl or heterocycloalkyl$C_{1-6}$alkyl, wherein heterocycloalkyl is N-containing monocyclic heterocycloalkyl;

or pharmaceutically acceptable salts, or enantiomers, or diastereomer thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{1-6}$alkoxy" denotes a group of the formula —O—R', wherein R' is a $C_{1-6}$alkyl group. Examples of $C_{1-6}$alkoxy moieties include methoxy, ethoxy, isopropoxy, and tert-butoxy. Particular "$C_{1-6}$alkoxy" groups are methoxy and ethoxy.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "halogen" means fluorine, chlorine, bromine or iodine.

The term "halo$C_{1-6}$alkyl" denotes a $C_{1-6}$alkyl group wherein at least one of the hydrogen atoms, of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "halo$C_{1-6}$alkyl" group is difluoromethyl or trifluoromethyl.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$cycloalkyl.

The term "carbonyl" alone or in combination refers to the group —C(O)—.

The term "cyano" alone or in combination refers to the group —CN.

The term "$C_{1-6}$alkylsulfanyl" denotes a group —S—R', wherein R' is a $C_{1-6}$alkyl group as defined above. Examples of $C_{1-6}$alkylsulfanyl include methylsulfanyl and ethylsulfanyl.

The term "$C_{1-6}$alkylsulfonyl" denotes a group —SO$_2$—R', wherein R' is a $C_{1-6}$alkyl group as defined above. Examples of $C_{1-6}$alkylsulfonyl include methylsulfonyl and ethylsulfonyl.

The term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl; piperidinyl, tetrahydropyranyl, tetrahydrothiopyranyl, piperazinyl, morpholinyl, 2-oxo-morpholinyl, 2-oxo-piperazinyl, thiomorpholinyl, 1,1-dioxo-thiomorpholin-4-yl, 1,1-dioxothiolanyl, azepanyl, diazepanyl, homopiperazinyl, or oxazepanyl. Particular "monocyclic heterocycloalkyl" groups are oxetanyl, tetrahydrofuranyl, tetrahydropyranyl, morpholinyl, pyrrolidinyl, 2-oxo-pyrrolidinyl, 2-oxo-morpholinyl and 2-oxo-piperazinyl.

The term "N-containing monocyclic heterocycloalkyl" is a "monocyclic heterocycloalkyl" as defined above wherein at least one of the heteroatoms is N. Examples for "N-containing monocyclic heterocycloalkyl" are aziridinyl, azetidinyl, pyrrolidinyl, 2-oxo-pyrrolidinyl, pyrazolidinyl, imidazolidinyl, oxazolidinyl, isoxazolidinyl, thiazolidinyl, piperidinyl, piperazinyl, morpholinyl, thiomorpholinyl, 1,1-dioxo-thiomorpholin-4-yl, azepanyl, diazepanyl, homopiperazinyl, or oxazepanyl. Particular "N-containing monocyclic heterocycloalkyl" groups are morpholinyl, pyrrolidinyl, 2-oxo-morpholinyl and 2-oxo-pyrrolidinyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention provides (i) novel compounds having the general formula I:

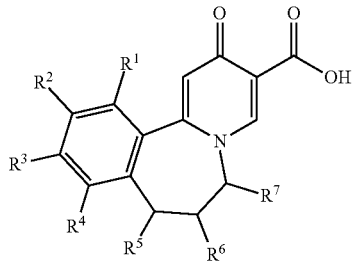

wherein
$R^1$, $R^2$, $R^3$ and $R^4$ are independently selected from $C_{1-6}$alkyl, halo$C_{1-6}$alkyl, hydrogen, halogen, amino, cyano, pyrrolidinyl and $OR^8$;
$R^5$, $R^6$, $R^7$ are independently selected from hydrogen, $C_{1-6}$alkyl or halo$C_{1-6}$alkyl; $R^8$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$alkyl; $C_{1-6}$alkoxy$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkoxycarbonylamino$C_{1-6}$alkyl; pyrazolyl$C_{1-6}$alkyl; triazolyl$C_{1-6}$alkyl or heterocycloalkyl$C_{1-6}$alkyl, wherein heterocycloalkyl is N-containing monocyclic heterocycloalkyl;
or pharmaceutically acceptable salts, or enantiomers, or diastereomer thereof.

Another embodiment of the present invention is (ii) a compound of formula I, wherein
$R^1$ is hydrogen;
$R^2$ is $C_{1-6}$alkoxy;
$R^3$ is $OR^8$, wherein $R^8$ is selected from $C_{1-6}$alkyl, halo$C_{1-6}$alkyl, phenyl$C_{1-6}$alky, $C_{1-6}$alkoxy$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl and $C_{1-6}$alkoxycarbonylamino$C_{1-6}$alkyl;
$R^4$ is hydrogen;
$R^5$ is hydrogen;
$R^6$ is hydrogen;
$R^7$ is hydrogen or $C_{1-6}$alkyl;
or pharmaceutically acceptable salts, or enantiomers, or diastereomer thereof.

A further embodiment of the present invention is (iii) a compound of formula I as defined above, wherein
$R^1$ is hydrogen;
$R^2$ is methoxy;
$R^3$ is methoxy, trifluoroethoxy, benzyloxy, methoxypropoxy, methylsulfanylpropoxy, methylsulfonylpropoxy, aminohexyloxy, methylcarbonylaminohexyloxy, methylsulfonylaminohexyloxy or tert-butoxycarbonylaminohexyloxy;
$R^4$ is hydrogen;
$R^5$ is hydrogen;
$R^6$ is hydrogen;
$R^7$ is hydrogen or ethyl;
or pharmaceutically acceptable salts, or enantiomers, or diastereomer thereof.

Another embodiment of the present invention is (iv) a compound of formula I as defined above, or pharmaceutically acceptable salts, or enantiomers, or diastereomer thereof, wherein $R^1$ is hydrogen; $R^2$ is $C_{1-6}$alkoxy; $R^4$ is hydrogen; R⁵ is hydrogen; R⁶ is hydrogen; and all remaining substituents have the significances given herein before.

A further embodiment of the present invention is (v) a compound of formula I as defined above, or pharmaceutically acceptable salts, or enantiomers, or diastereomer thereof, wherein R¹ is hydrogen; R² is methoxy; R⁴ is hydrogen; R⁵ is hydrogen; R⁶ is hydrogen; and all remaining substituents have the significances given herein before.

Another embodiment of the present invention is (vi) a compound of formula I as defined above, or pharmaceutically acceptable salts, or enantiomers, or diastereomer thereof, wherein R³ is OR⁸, wherein R⁸ is $C_{1-6}$alkoxy-$C_{1-6}$alkyl, $C_{1-6}$alkylsulfanyl$C_{1-6}$alkyl, $C_{1-6}$alkylsulfonylamino$C_{1-6}$alkyl or $C_{1-6}$alkoxycarbonylamino$C_{1-6}$alkyl; and all remaining substituents have the significances given herein before.

A further embodiment of the present invention is (vii) a compound of formula I as defined above, or pharmaceutically acceptable salts, or enantiomers, or diastereomer, or diastereomer thereof, wherein R³ is methoxypropoxy, methylsulfanylpropoxy, methylsulfonylaminohexyloxy or tert-butoxycarbonylaminohexyloxy; and all remaining substituents have the significances given herein before.

Another embodiment of the present invention is (viii) a compound of formula I as defined above, or pharmaceutically acceptable salts, or enantiomers, or diastereomer thereof, wherein R⁷ is $C_{1-6}$alkyl; and all remaining substituents have the significances given herein before. A further embodiment of the present invention is (ix) a compound of formula I as defined above, or pharmaceutically acceptable salts, or enantiomers, or diastereomer thereof, wherein R⁷ is ethyl; and all remaining substituents have the significances given herein before.

Particular compounds of formula I according to the invention are the following:

10,11-Dimethoxy-2-oxo-7,8-dihydro-6H-pyrido[2,1-a][2]benzazepine-3-carboxylic acid;

10-Benzyloxy-6-ethyl-11-methoxy-2-oxo-7,8-dihydro-6H-pyrido[2,1-a][2]benzazepine-3-carboxylic acid;

6-Ethyl-11-methoxy-10-(3-methoxypropoxy)-2-oxo-7,8-dihydro-6H-pyrido[2,1-a][2]benzazepine-3-carboxylic acid;

10-[6-(Tert-butoxycarbonylamino)hexoxy]-6-ethyl-11-methoxy-2-oxo-7,8-dihydro-6H-pyrido[2,1-a][2]benzazepine-3-carboxylic acid;

10-(6-Aminohexoxy)-6-ethyl-11-methoxy-2-oxo-7,8-dihydro-6H-pyrido[2,1-a][2]benzazepine-3-carboxylic acid;

10-(6-Acetamidohexoxy)-6-ethyl-11-methoxy-2-oxo-7,8-dihydro-6H-pyrido[2,1-a][2]benzazepine-3-carboxylic acid;

6-Ethyl-10-[6-(methanesulfonamido)hexoxy]-11-methoxy-2-oxo-7,8-dihydro-6H-pyrido[2,1-a][2]benzazepine-3-carboxylic acid;

6-Ethyl-11-methoxy-10-(3-methylsulfanylpropoxy)-2-oxo-7,8-dihydro-6H-pyrido[2,1-a][2]benzazepine-3-carboxylic acid;

6-Ethyl-11-methoxy-10-(3-methylsulfonylpropoxy)-2-oxo-7,8-dihydro-6H-pyrido[2,1-a][2]benzazepine-3-carboxylic acid;

6-Ethyl-11-methoxy-2-oxo-10-(2,2,2-trifluoroethoxy)-7,8-dihydro-6H-pyrido[2,1-a][2]benzazepine-3-carboxylic acid;

or pharmaceutically acceptable salts, or enantiomers, or diastereomer thereof.

More particularly, the invention relates to the following compounds of formula I:

6-Ethyl-11-methoxy-10-(3-methoxypropoxy)-2-oxo-7,8-dihydro-6H-pyrido[2,1-a][2]benzazepine-3-carboxylic acid;

6-Ethyl-10-[6-(methanesulfonamido)hexoxy]-1-methoxy-2-oxo-7,8-dihydro-6H-pyrido[2,1-a][2]benzazepine-3-carboxylic acid;

6-Ethyl-11-methoxy-2-oxo-10-(2,2,2-trifluoroethoxy)-7,8-dihydro-6H-pyrido[2,1-a][2]benzazepine-3-carboxylic acid;

or pharmaceutically acceptable salts, or enantiomers thereof.

Synthesis

The compounds of the present invention can be prepared by any conventional means. Suitable processes for synthesizing these compounds as well as their starting materials are provided in the schemes below and in the examples. All substituents, in particular, R¹ to R⁷ are as defined above unless otherwise indicated. Furthermore, and unless explicitly otherwise stated, all reactions, reaction conditions, abbreviations and symbols have the meanings well known to a person of ordinary skill in organic chemistry.

General synthetic route for Compounds I (Scheme 1)

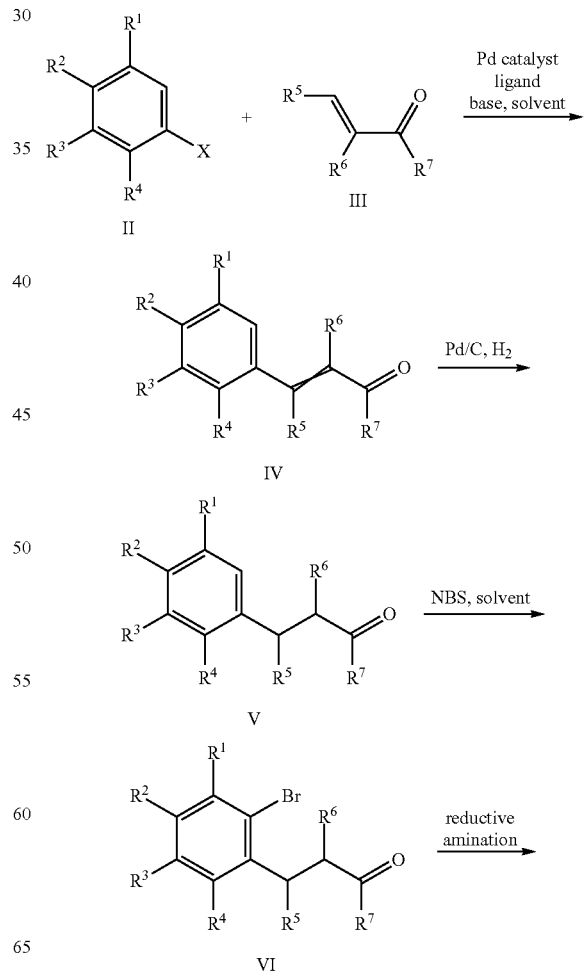

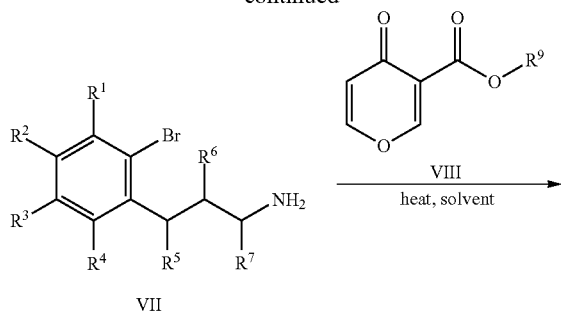
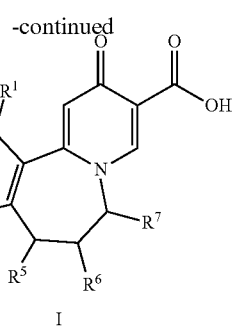

X is Br, I or OS(O)$_2$CF$_3$;
R$^9$ is C$_{1-6}$alkyl

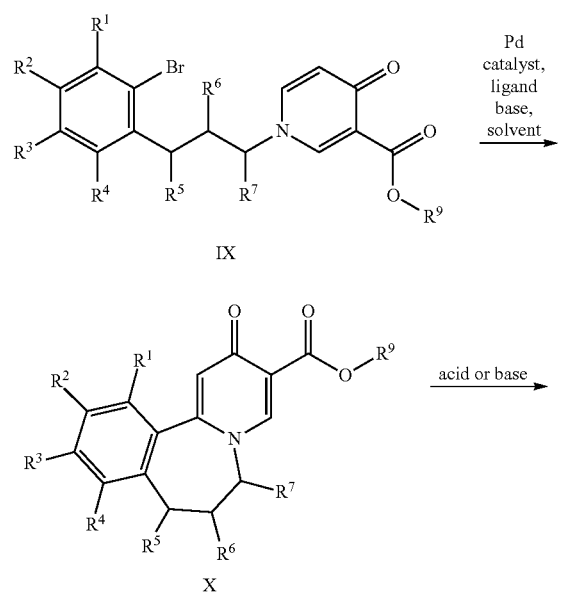

The compound of formula I can be prepared according to Scheme 1. Coupling reaction of substituted benzene II with enal or enone III affords Compound IV. The reaction can be carried out in the presence of a Pd catalyst such as Pd(OAc)$_2$, a ligand such as PPh$_3$, and a suitable base such as triethyl amine or K$_2$CO$_3$, in a suitable solvent such as DMF or toluene at a temperature between room temperature and 130° C. Compound IV is hydrogenated under a hydrogen atmosphere in the presence of Pd/C in a solvent such as methanol to give Compound V. Compound V reacts with NBS in a solvent such as ethyl acetate to give Compound VI, which undergoes reductive amination to form Compound VII. Compound VII is heated with Compound VIII in a solvent such as ethanol to give Compound IX. Compound X is obtained by cyclization of IX by using a Pd catalyzed reaction. Hydrolyzation of Compound X with an acid such as TFA or HCl in a suitable solvent such as DCM, or with a base such as lithium hydroxide in a suitable solvent such as EtOH/H$_2$O or MeOH/H$_2$O affords the compound of formula I.

General Synthetic Route for Compounds I-1
(Scheme 2)

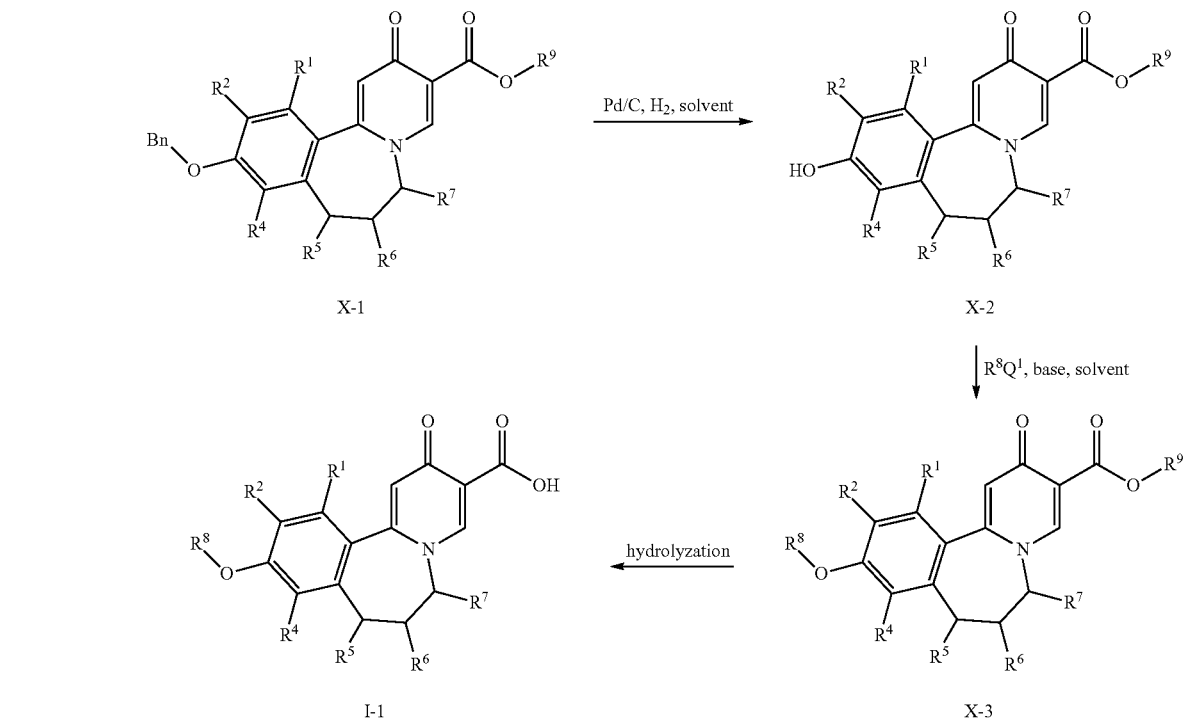

$Q^1$ is halogen, $OS(O)_2CH_3$ or $OS(O)_2(4\text{-}CH_3\text{-Ph})$.

$R^9$ is $C_{1-6}$alkyl

The compound of formula I-1 can be prepared according to Scheme 2. Debenzylation of Compound X-1 by hydrogenation is carried out in the presence of Pd/C in a solvent such as methanol or THF to afford Compound X-2. Then Compound X-2 reacts with halide, mesylate or tosylate in the presence of a base such as $K_2CO_3$ in a solvent such as acetone or DMF to give X-3. Hydrolyzation of Compound X-3 with an acid such as TFA or HCl in a suitable solvent such as DCM, or with a base such as lithium hydroxide in a suitable solvent such as $EtOH/H_2O$ or $MeOH/H_2O$ affords the compound of formula I-1.

This invention also relates to a process for the preparation of a compound of formula I comprising (a) hydrolysis of a compound of formula (A) by using an acid or a base

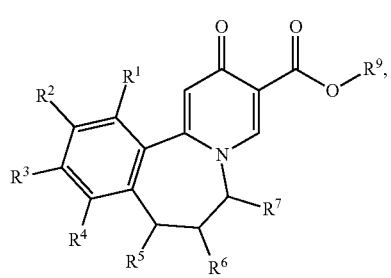

(A)

or (b) hydrolysis of a compound of formula (B) by using an acid or a base

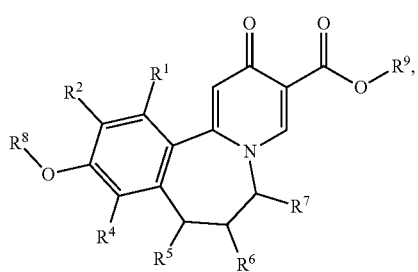

(B)

wherein $R^1$ to $R^9$ are defined above unless otherwise indicated.

In step (a) and (b), an acid is for example TFA or HCl; a base is for example lithium hydroxide or sodium hydroxide.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, *Williams & Wilkins*, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of a HBV infection. The invention further relates to a method for the treatment of a HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
DMF: dimethylformamide
DMSO-d6: deuterated dimethylsulfoxide
EtOAc: ethyl acetate
h or hr: hour
hrs: hours
$IC_{50}$: the half maximal inhibitory concentration
NBS: N-bromosuccinimide
HPLC: high performance liquid chromatography
LC/MS: Liquid chromatography/mass spectrometry
METHANOL-$d_4$: perdeuteromethanol
M: molarity
MHz: megahertz
min: minute
mM: millimoles per liter
mmol: millimole
MS (ESI): mass spectroscopy (electron spray ionization)
NMR: nuclear magnetic resonance
rt: room temperature
$PPh_3$: triphenylphosphine
Pd/C: palladium on activated carbon
prep-HPLC: preparative high performance liquid chromatography
TFA: trifluoroacetic acid
δ: chemical shift
t-BuOK: potassium tert-butylate General Experimental Conditions Intermediates and final compounds were purified by flash chromatography using one of the following instruments: i) Biotage SPI system and the Quad 12/25 Cartridge module. ii) ISCO combi-flash chromatography instrument. Silica gel Brand and pore size: i) KP-SIL 60 Å, particle size: 40-60 m;

ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column, SunFire™ Perp $C_{18}$ (5 μm, OBD™ 30×100 mm) column, Phenomenex Synergi Max-RP (4 μm, 30×150 mm) column or Phenomenex Gemini C18 (10 μm, 25×150 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3$—$H_2O$ in $H_2O$; B: acetonitrile;

Neutral condition: A: $H_2O$; B: acetonitrile.

LC/MS spectra were also obtained using a SHIMADZU, LCMS-2020 and SHIMADZU LC20AB with UV DAD or Agilent G 1956A and Agilent 1200 Series LC; UV DAD. Standard LC/MS conditions were as follows (running time 3 minutes):

Acidic condition: A: 0.0375% TFA in water (V/V); B: 0.01875% TFA in acetonitrile (V/V)

Basic condition: A: 0.05% $NH_3H_2O$ in water (V/V); B: acetonitrile

Neutral condition: A: water; B: acetonitrile

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover, NMR Spectra were obtained using Bruker Avance 400 MHz or 300 MHz.

All reactions involving air-sensitive reagents were performed under an argon atmosphere. Reagents were used as received from commercial suppliers without further purification unless otherwise noted.

PREPARATIVE EXAMPLES

Example 1: 10,11-Dimethoxy-2-oxo-7,8-dihydro-6H-pyrido[2,1-a][2]benzazepine-3-carboxylic acid

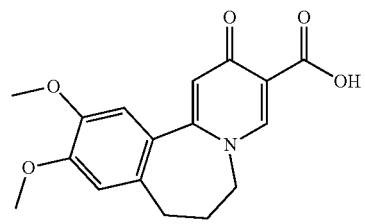 [SMILES: COc1cc2c(cc1OC)-c1cc(=O)c(C(=O)O)cn1CCC2]

Step 1: Preparation of N-[3-(3,4-dimethoxyphenyl)propyl]formamide

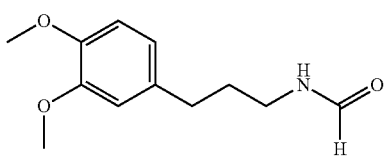 [SMILES: COc1ccc(CCCNC=O)cc1OC]

A mixture of 3-(3, 4-dimethoxyphenyl)propan-1-amine (1.95 g, 10 mmol) and ethyl formate (20 mL) was refluxed for 16 hrs. Then the mixture was concentrated under reduced pressure and the residue was purified by column chromatography to give N-[3-(3,4-dimethoxyphenyl)propyl]formamide (1.5 g).

Step 2: Preparation of 7,8-dimethoxy-4,5-dihydro-3H-2-benzazepine

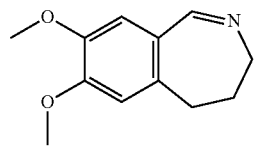

To a solution of N-[3-(3,4-dimethoxyphenyl)propyl]formamide (224 mg, 1 mmol) in $CH_2Cl_2$ under nitrogen was added oxalyl chloride (140 mg, 1.1 mmol). The solution was stirred at rt for 30 mins, then cooled to −10° C. To the cooled reaction mixture was added iron(II) chloride (180 mg, 1.1 mmol). The resulting mixture was allowed to warm to rt and stirred for 24 hrs. Then the reaction was quenched by addition of 2 M hydrochloric acid (10 mL), and the resulting biphasic mixture was stirred at rt for 1 hr. Then the organic layer was separated, washed with brine, dried over anhydrous $Na_2SO_4$ and concentrated under reduced pressure to give a dark oil. To the oil was added a solution of concentrated $H_2SO_4$ (0.5 mL) in MeOH (9.5 mL). The resulting mixture was refluxed for 20 hrs, then cooled to rt and concentrated under reduced pressure. The dark red residue was partitioned between $H_2O$ (5 mL) and EtOAc (30 mL). The organic layer was separated and washed with 2 M hydrochloric acid twice. The combined aqueous and acidic washings were basified with aqueous ammonia and then extracted with $CH_2Cl_2$ (10 mL) for three times. The combined organic layers were washed with brine (10 mL), dried over anhydrous $Na_2SO_4$ and concentrated under reduced pressure. The residue was purified by column chromatography to give 7,8-dimethoxy-4,5-dihydro-3H-2-benzazepine.

Step 3: Preparation of ethyl 10,11-dimethoxy-2-oxo-6,7,8,12b-tetrahydro-1H-pyrido[2,1-a][2]benzazepine-3-carboxylate

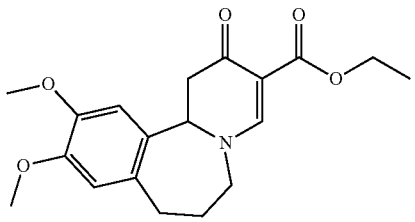 [SMILES: CCOC(=O)C1=CN2CCCc3cc(OC)c(OC)cc3C2CC1=O]

To a solution of 7,8-dimethoxy-4,5-dihydro-3H-2-benzazepine (412 mg, 2 mmol) in t-BuOH (7 mL) was added ethyl-2-(N, N-dimethylaminomethylene)-3-oxo-butanoate (1.02 g, 6 mmol). The mixture was heated at 150° C. under microwave for 120 mins. The mixture was concentrated under reduced pressure, and the residue was dissolved in $CH_2Cl_2$. The organic solution was washed with 5% hydrochloric acid and brine, dried over anhydrous Na$_2$SO$_4$ and concentrated under reduced pressure. The residue was purified by column chromatography to give ethyl 10,11-dimethoxy-2-oxo-6,7,8,12b-tetrahydro-1H-pyrido[2,1-a][2]benzazepine-3-carboxylate (246 mg).

Step 4: Preparation of ethyl 10,11-dimethoxy-2-oxo-7,8-dihydro-6H-pyrido[2,1-a][2]benzazepine-3-carboxylate

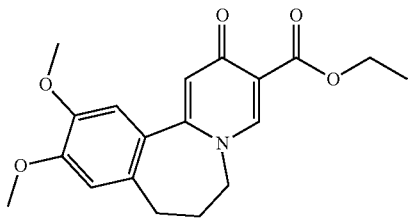 [SMILES: CCOC(=O)c1cn2c(cc1=O)-c1cc(OC)c(OC)cc1CCC2]

A mixture of ethyl 10,11-dimethoxy-2-oxo-7,8-dihydro-6H-pyrido[2,1-a][2]benzazepine-3-carboxylate (300 mg, 0.84 mmol) and p-chloranil (300 mg, 1.2 mmol) in dimethoxyethane and toluene (40 mL, V/V=1/1) was refluxed for 2 hrs. After being cooled to room temperature, the reaction mixture was concentrated under reduced pressure. The residue was purified by flash column chromatography to give ethyl 10,11-dimethoxy-2-oxo-7,8-dihydro-6H-pyrido[2,1-a][2]benzazepine-3-carboxylate as a yellow solid (200 mg).

Step 5: Preparation of 10,11-dimethoxy-2-oxo-7,8-dihydro-6H-pyrido[2,1-a][2]benzazepine-3-carboxylic acid

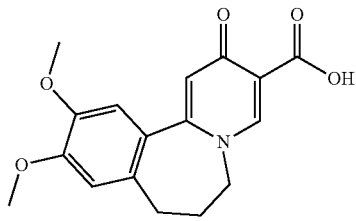 [SMILES: COc1cc2c(cc1OC)-c1cc(=O)c(C(=O)O)cn1CCC2]

To a solution of ethyl 10,11-dimethoxy-2-oxo-7,8-dihydro-6H-pyrido[2,1-a][2]benzazepine-3-carboxylate (200 mg, 0.52 mmol) in methanol and water (20 mL, V/V=1) was added lithium hydroxide monohydrate (480 mg) at rt. The resulting mixture was heated at 80° C. with stirring for 10 mins, then acidified to pH=1-2 with 2 M hydrochloric acid and extracted with CH$_2$Cl$_2$ (10 mL) twice. The combined organic layers were washed with brine, dried over anhydrous Na$_2$SO$_4$ and concentrated under reduced pressure. The residue was purified by prep-HPLC to give 10,11-dimethoxy-2-oxo-7,8-dihydro-6H-pyrido[2,1-a][2]benzazepine-3-carboxylic acid (7 mg). $^1$H NMR (400 MHz, DMSO-d$_6$) δ ppm 8.91 (s, 1H), 7.16 (s, 1H), 7.02 (s, 1H), 6.91 (s, 1H), 4.42 (b, 1H), 3.84 (d, 6H), 3.74 (br. s., 1H), 3.32 (br.s., 1H), 2.52 (br.s., 1H), 2.0 (br.s., 1H), 1.83 (br.s., 1H). MS obsd. (ESI$^+$) [(M+H)$^+$]: 316.

Example 2: 10-Benzyloxy-6-ethyl-11-methoxy-2-oxo-7,8-dihydro-6H-pyrido[2,1-a][2]benzazepine-3-carboxylic acid

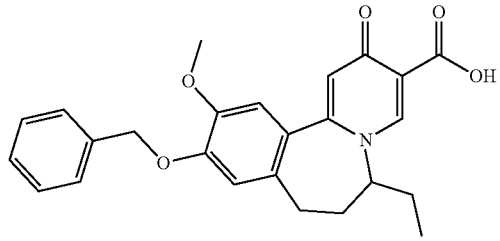 [SMILES: CCC1CCc2cc(OCc3ccccc3)c(OC)cc2-c2cc(=O)c(C(=O)O)cn21]

Step 1: Preparation of 1-(3-hydroxy-4-methoxy-phenyl)pent-1-en-3-one

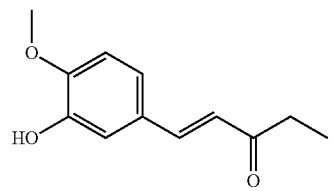

A mixture of 5-bromo-2-methoxyphenol (30.0 g, 0.15 mol), ethyl vinyl ketone (24.8 g, 0.30 mol), Et$_3$N (44.9 g, 0.44 mol), PPh$_3$ (3.9 g, 0.015 mol) and Pd(OAc)$_2$ (1.7 g, 7.4 mmol) in DMF (400 mL) was heated at 110° C. with stirring under nitrogen for 16 hrs. After being cooled to rt, the mixture was filtered. The filtrate was partitioned between EtOAc (50 mL) and brine (20 mL). The organic layer was separated, dried over anhydrous Na$_2$SO$_4$ and concentrated under reduced pressure. The residue was purified by flash column chromatography to give 1-(3-hydroxy-4-methoxy-phenyl)pent-1-en-3-one (20.0 g) as a light yellow solid.

Step 2: Preparation of 1-(3-hydroxy-4-methoxy-phenyl)pentan-3-one

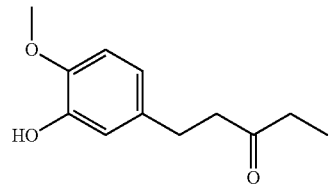

A mixture of 1-(3-hydroxy-4-methoxy-phenyl)pent-1-en-3-one (20.0 g, 0.097 mol) and Pd/C (2.0 g) in MeOH (200 mL) was stirred under hydrogen (50 psi) at 25° C. for 24 hrs. The mixture was filtered, and the filtrate was concentrated under reduced pressure to give 1-(3-hydroxy-4-methoxy-phenyl)pentan-3-one (24.0 g) as a yellow oil which was used in the next step without further purification.

Step 3: Preparation of 1-(3-benzyloxy-4-methoxy-phenyl)pentan-3-one

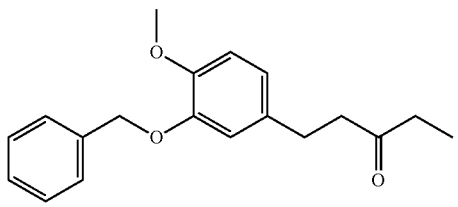 [SMILES: CCC(=O)CCc1ccc(OC)c(OCc2ccccc2)c1]

A mixture of 1-(3-hydroxy-4-methoxy-phenyl)pentan-3-one (24.0 g, 0.092 mol), K$_2$CO$_3$ (15.3 g, 0.11 mol) and bromomethylbenzene (17.3 g, 0.10 mol) in acetone (250 mL) was heated at 60° C. with stirring for 16 hrs. After being cooled to rt, the mixture was filtered. The filtrate was concentrated under reduced pressure, and the residue was purified by flash column chromatography to give 1-(3-benzyloxy-4-methoxy-phenyl)pentan-3-one (15.8 g) as a light yellow oil.

Step 4: Preparation of 1-(5-benzyloxy-2-bromo-4-methoxy-phenyl)pentan-3-one

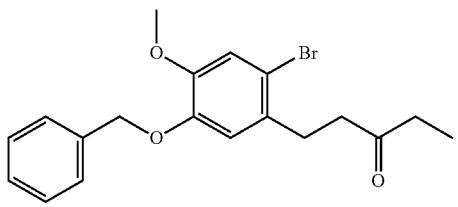 [SMILES: CCC(=O)CCc1cc(OCc2ccccc2)c(OC)cc1Br]

A stirred solution of 1-(3-benzyloxy-4-methoxy-phenyl)pentan-3-one (14.2 g, 47.6 mmol) in EtOAc (150 mL) was cooled to 0-5° C., then to the cooled solution was added NBS (8.9 g, 50.0 mmol) portion wise. The resulting mixture was stirred at 5° C. for 3 hrs, and then concentrated under reduced pressure. The residue was purified by flash column chromatography to give 1-(5-benzyloxy-2-bromo-4-methoxy-phenyl)pentan-3-one (13.5 g) as a white solid.

Step 5: Preparation of 1-(5-benzyloxy-2-bromo-4-methoxy-phenyl)pentan-3-amine

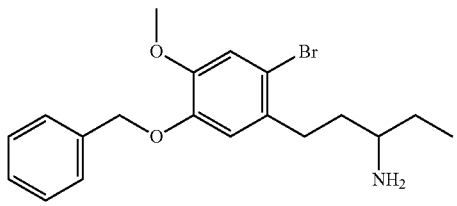 [SMILES: CCC(N)CCc1cc(OCc2ccccc2)c(OC)cc1Br]

A mixture of 1-(5-benzyloxy-2-bromo-4-methoxy-phenyl)pentan-3-one (13.5 g, 36.8 mmol) and NH$_4$OAc (19.3 g, 250.5 mmol) in MeOH (300 mL) was heated at 40° C. with stirring for 4 hrs, then cooled to 10° C. To the above mixture was added NaBH$_3$CN (3.4 g, 53.7 mmol) portion wise. The resulting mixture was allowed to warm to 25° C. and stirred at 25° C. for 16 hrs. The mixture was concentrated under reduced pressure, and the residue was diluted with EtOAc (500 mL). The organic solution was washed successively with 4 M hydrochloric acid, saturated Na$_2$CO$_3$ aqueous solution and brine, then dried over anhydrous Na$_2$SO$_4$ and concentrated under reduced pressure to give crude 1-(5-benzyloxy-2-bromo-4-methoxy-phenyl)pentan-3-amine (13.0 g) as a colorless oil which was used in the next step without further purification.

Step 6: Preparation of tert-butyl 2-(dimethylaminomethylene)-3-oxo-butanoate

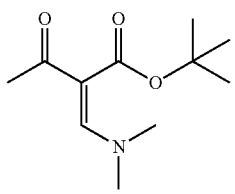

To a stirred solution of tert-butyl 3-oxobutanoate (30.0 g, 0.19 mol) in 1, 4-dioxane (500 mL) was added N,N-dimethylformamide dimethyl acetal (113.0 g, 0.95 mol). The resulting mixture was stirred at 25° C. for 16 hrs, and then concentrated under reduced pressure. The residue was diluted with H$_2$O (300 mL), and extracted with EtOAc (200 mL) for three times. The combined organic layers were dried over anhydrous Na$_2$SO$_4$ and concentrated under reduced pressure to give crude tert-butyl 2-(dimethylaminomethylene)-3-oxo-butanoate (40.0 g) as a dark yellow liquid which was used in the next step without further purification.

Step 7: Preparation of tert-butyl 4-oxopyran-3-carboxylate

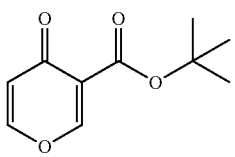

To a stirred solution of tert-butyl 2-(dimethylaminomethylene)-3-oxo-butanoate (40.0 g, 0.19 mol) and ethyl formate (27.8 g, 0.36 mol) in THF (700 mL) was added t-BuOK (52.6 g, 0.47 mol) portion wise at 0° C. Then the mixture was allowed to warm to 25° C. and stirred at same temperature for 16 hrs. Then the reaction was quenched by adding 1 M hydrochloric acid. The resulting mixture was extracted with EtOAc (200 mL) for three times. The combined organic layers were washed with saturated NaHCO$_3$ aqueous solution and brine, dried over anhydrous Na$_2$SO$_4$, and concentrated under reduced pressure. The residue was purified by the flash column chromatography to give tert-butyl 4-oxopyran-3-carboxylate (9.5 g) as a dark yellow solid.

Step 8: Preparation of tert-butyl 1-[3-(5-benzyloxy-2-bromo-4-methoxy-phenyl)-1-ethyl-propyl]-4-oxo-pyridine-3-carboxylate

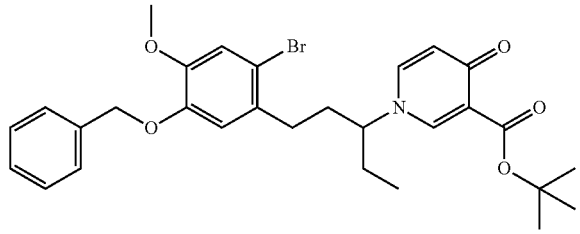 [SMILES: CCC(CCc1cc(OCc2ccccc2)c(OC)cc1Br)n1ccc(=O)c(C(=O)OC(C)(C)C)c1]

A mixture of 1-(5-benzyloxy-2-bromo-4-methoxy-phenyl)pentan-3-amine (2.0 g, 5.29 mmol) and tert-butyl 4-oxopyran-3-carboxylate (1.0 g, 5.29 mmol) in EtOH (30 mL) was heated at 80° C. with stirring for 16 hrs. The mixture was concentrated under reduced pressure and the residue was purified by the flash column chromatography to give tert-butyl 1-[3-(5-benzyloxy-2-bromo-4-methoxy-phenyl)-1-ethyl-propyl]-4-oxo-pyridine-3-carboxylate (720 mg) as a yellow oil.

Step 9: Preparation of tert-butyl 10-benzyloxy-6-ethyl-11-methoxy-2-oxo-7,8-dihydro-6H-pyrido[2,1-a][2]benzazepine-3-carboxylate

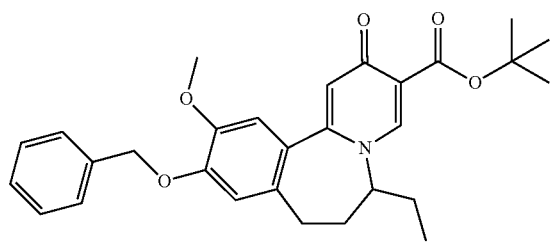 [SMILES: CCC1CCc2cc(OCc3ccccc3)c(OC)cc2-c2cc(=O)c(C(=O)OC(C)(C)C)cn21]

A mixture of tert-butyl 1-[3-(5-benzyloxy-2-bromo-4-methoxy-phenyl)-1-ethyl-propyl]-4-oxo-pyridine-3-carboxylate (720 mg, 1.29 mmol), KOAc (190 mg, 1.94 mmol) and chloro[(tri-tert-butylphosphine)-2-(2-aminobiphenyl)]palladium(II) (46 mg, 0.13 mmol) in DMA (7 mL) was heated at 120° C. with stirring under nitrogen for 12 hrs. After being cooled to rt, the mixture was partitioned between water and EtOAc. The organic layer was separated, washed with water, dried over anhydrous $Na_2SO_4$, and concentrated under reduced pressure. The residue was purified by the flash column chromatography to give tert-butyl 10-benzyloxy-6-ethyl-11-methoxy-2-oxo-7,8-dihydro-6H-pyrido[2,1-a][2]benzazepine-3-carboxylate (190 mg).

Step 10: Preparation of 10-benzyloxy-6-ethyl-11-methoxy-2-oxo-7,8-dihydro-6H-pyrido[2,1-a][2]benzazepine-3-carboxylic acid

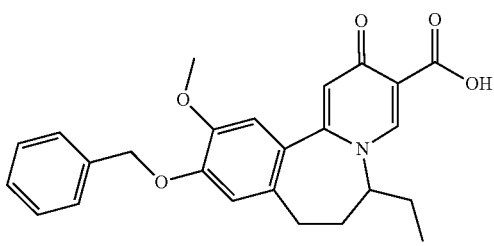 [SMILES: CCC1CCc2cc(OCc3ccccc3)c(OC)cc2-c2cc(=O)c(C(=O)O)cn21]

A solution of tert-butyl 10-benzyloxy-6-ethyl-11-methoxy-2-oxo-7,8-dihydro-6H-pyrido[2,1-a][2]benzazepine-3-carboxylate (110 mg, 0.11 mmol) in 2,2,2-trifluoroacetic acid (0.5 mL) and DCM (1 mL) was stirred at 20° C. for 16 hrs. The resulting mixture was partitioned between DCM and water. The organic layer was separated, washed with water and brine, dried over anhydrous $Na_2SO_4$, and concentrated under reduced pressure. The residue was purified by recrystallization from DMSO and $CH_3CN$ to give 10-benzyloxy-6-ethyl-11-methoxy-2-oxo-7,8-dihydro-6H-pyrido[2,1-a][2]benzazepine-3-carboxylic acid (7 mg) as a light yellow solid. $^1$H NMR (400 MHz, CDCl$_3$) δ ppm 8.60 (s, 1H), 7.32-7.50 (m, 5H), 7.00 (s, 1H), 6.73-6.83 (m, 2H), 5.14-5.27 (m, 2H), 3.94 (s, 3H), 2.58-2.68 (m, 2H), 2.43-2.55 (m, 1H), 1.92-2.16 (m, 1H), 0.97 (t, 3H), MS obsd. (ESI$^+$) [(M+H)$^+$]: 420.

Example 3: 6-Ethyl-11-methoxy-10-(3-methoxy-propoxy)-2-oxo-7,8-dihydro-6H-pyrido[2,1-a][2]benzazepine-3-carboxylic acid

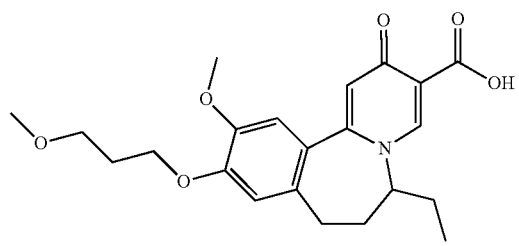 [SMILES: CCC1CCc2cc(OCCCOC)c(OC)cc2-c2cc(=O)c(C(=O)O)cn21]

Step 1: Preparation of 10-benzyloxy-6-ethyl-11-methoxy-2-oxo-7,8-dihydro-6H-pyrido[2,1-a][2]benzazepine-3-carboxylic acid

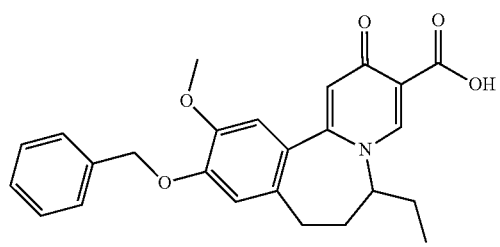 [SMILES: CCC1CCc2cc(OCc3ccccc3)c(OC)cc2-c2cc(=O)c(C(=O)O)cn21]

A mixture of tert-butyl 1-[3-(5-benzyloxy-2-bromo-4-methoxy-phenyl)-1-ethyl-propyl]-4-oxo-pyridine-3-carboxylate (15.0 g, 0.027 mol), KOAc (7.9 g, 0.08 mol) and chloro[(tri-tert-butylphosphine)-2-(2-aminobiphenyl)]palladium(II) (1.4 g, 0.003 mmol) in DMA (150 mL) was heated at 150° C. with stirring under nitrogen for 24 hrs. After being cooled to rt, the mixture was partitioned between EtOAc and brine. The separated organic layer was washed with brine, dried over anhydrous $Na_2SO_4$ and concentrated under reduced pressure. The reaction was repeated in the same scale and worked up with the same procedure as described above. Then the combined residue was purified by the flash column chromatography to give 10-benzyloxy-6-ethyl-11-methoxy-2-oxo-7,8-dihydro-6H-pyrido[2,1-a][2]benzazepine-3-carboxylic acid (28.54 g, crude) as a dark red oil, which was used in the next step without further purification.

Step 2: Preparation of methyl 10-benzyloxy-6-ethyl-11-methoxy-2-oxo-7,8-dihydro-6H-pyrido[2,1-a][2]benzazepine-3-carboxylate

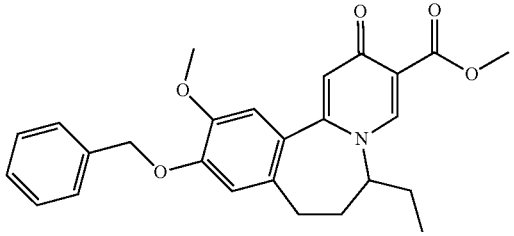 [SMILES: CCC1CCc2cc(OCc3ccccc3)c(OC)cc2-c2cc(=O)c(C(=O)OC)cn21]

To a stirred solution of 10-benzyloxy-6-ethyl-11-methoxy-2-oxo-7,8-dihydro-6H-pyrido[2,1-a][2]benzazepine-3-carboxylic acid (28.54 g, 0.068 mol) in MeOH (300 mL) was added SOCl$_2$ (9.71 g, 0.082 mol) at 15° C. Then the mixture was heated at 70° C. with stirring for 12 hrs. After being cooled to rt, the mixture was concentrated under reduced pressure. The residue was partitioned between DCM and water. The organic layer was washed with brine, dried over anhydrous Na$_2$SO$_4$, and concentrated under reduced pressure. The residue was purified by prep-HPLC to give methyl 10-benzyloxy-6-ethyl-11-methoxy-2-oxo-7,8-dihydro-6H-pyrido[2,1-a][2]benzazepine-3-carboxylate (1.86 g) as a yellow solid.

Step 3: Preparation of methyl 6-ethyl-10-hydroxy-11-methoxy-2-oxo-7,8-dihydro-6H-pyrido[2,1-a][2]benzazepine-3-carboxylate

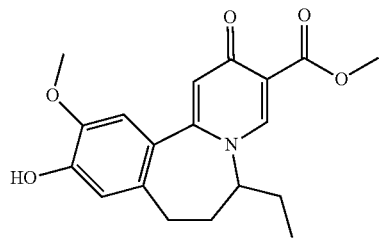 [SMILES: CCC1CCc2cc(O)c(OC)cc2-c2cc(=O)c(C(=O)OC)cn21]

A mixture of methyl 10-benzyloxy-6-ethyl-11-methoxy-2-oxo-7,8-dihydro-6H-pyrido[2,1-a][2]benzazepine-3-carboxylate (890 mg, 2.05 mmol) and Pd/C (100 mg) in MeOH (20 mL) was stirred under hydrogen (15 psi) at 15° C. for 16 hrs. The mixture was filtered, and the filtrate was concentrated under reduced pressure to give methyl 6-ethyl-10-hydroxy-11-methoxy-2-oxo-7,8-dihydro-6H-pyrido[2,1-a][2]benzazepine-3-carboxylate (650 mg) as a yellow solid, which was used in the next step without further purification.

Step 4: Preparation of methyl 6-ethyl-11-methoxy-10-(3-methoxypropoxy)-2-oxo-7,8-dihydro-6H-pyrido[2,1-a][2]benzazepine-3-carboxylate

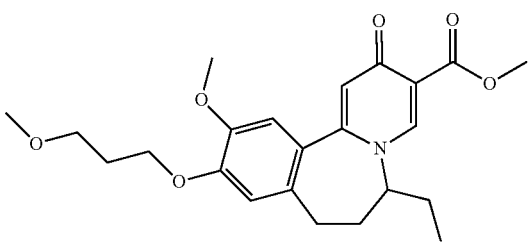

A mixture of methyl 6-ethyl-10-hydroxy-11-methoxy-2-oxo-7,8-dihydro-6H-pyrido[2,1-a][2]benzazepine-3-carboxylate (240 mg, 0.70 mmol), 1-bromo-3-methoxy-propane (107 mg, 0.70 mmol) and K$_2$CO$_3$ (145 mg, 1.05 mmol) in DMF (5 mL) was heated at 70° C. with stirring for 16 hrs. After being cooled to rt, the mixture was diluted with H$_2$O (10 mL) and extracted with EtOAc (20 mL) for three times. The combined organic layers were dried over anhydrous Na$_2$SO$_4$ and concentrated under reduced pressure to give crude methyl 6-ethyl-11-methoxy-10-(3-methoxypropoxy)-2-oxo-7,8-dihydro-6H-pyrido[2,1-a][2]benzazepine-3-carboxylate (200 mg) which was used in the next step without further purification.

Step 5: Preparation of 6-ethyl-11-methoxy-10-(3-methoxypropoxy)-2-oxo-7,8-dihydro-6H-pyrido[2,1-a][2]benzazepine-3-carboxylic acid

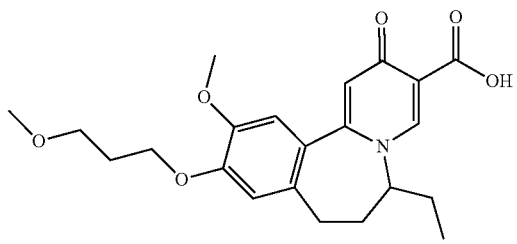 [SMILES: CCC1CCc2cc(OCCCOC)c(OC)cc2-c2cc(=O)c(C(=O)O)cn21]

A solution of methyl 6-ethyl-11-methoxy-10-(3-methoxypropoxy)-2-oxo-7,8-dihydro-6H-pyrido[2,1-a][2]benzazepine-3-carboxylate (200 mg, 0.11 mmol) and NaOH (9 mg, 0.22 mmol) in MeOH (2 mL) and water (0.1 mL) was stirred at 15° C. for 12 hrs. Then the mixture was acidified with 1 M hydrochloric acid to pH=3-4. The resulting mixture was concentrated under reduced pressure, and the residue was purified by prep-HPLC to give 6-ethyl-11-methoxy-10-(3-methoxypropoxy)-2-oxo-7,8-dihydro-6H-pyrido[2,1-a][2]benzazepine-3-carboxylic acid (5 mg) as a white solid. $^1$H NMR (400 MHz, CD$_3$OD) δ ppm 8.73 (s, 1H), 7.16 (s, 1H), 6.96 (s, 1H), 6.85 (s, 1H), 4.16 (t, 2H), 3.90 (s, 3H), 3.60 (t, 2H), 3.36 (s, 3H), 2.72 (br. s., 1H), 2.26-2.58 (m, 2H), 1.87-2.22 (m, 6H), 0.94 (s, 3H). MS obsd. (ESI) [(M+H)$^+$]: 402.

Example 4: 10-[6-(Tert-butoxycarbonylamino)hexoxy]-6-ethyl-11-methoxy-2-oxo-7,8-dihydro-6H-pyrido[2,1-a][2]benzazepine-3-carboxylic acid

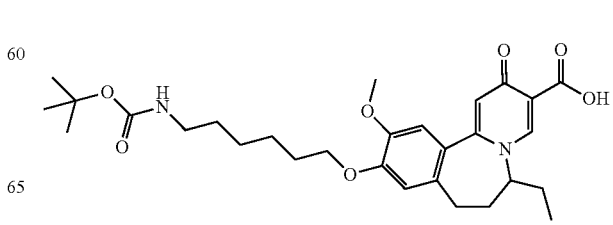

Step 1: Preparation of methyl 10-[6-(tert-butoxycarbonylamino)hexoxy]-6-ethyl-11-methoxy-2-oxo-7,8-dihydro-6H-pyrido[2,1-a][2]benzazepine-3-carboxylate

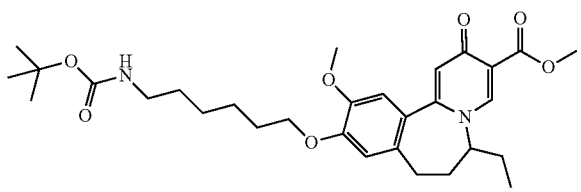 [SMILES: CCC1CCc2cc(OCCCCCCNC(=O)OC(C)(C)C)c(OC)cc2-c2cc(=O)c(C(=O)OC)cn21]

A mixture of methyl 6-ethyl-10-hydroxy-11-methoxy-2-oxo-7,8-dihydro-6H-pyrido[2,1-a][2]benzazepine-3-carboxylate (120 mg, 0.35 mmol), tert-butyl N-(6-bromohexyl) carbamate (147 mg, 0.52 mmol) and K$_2$CO$_3$ (87 mg, 0.63 mmol) in DMF (3 mL) was heated at 70° C. with stirring for 12 hrs. After being cooled to rt, the mixture was partitioned between H$_2$O and EtOAc. The aqueous layer was extracted with EtOAc twice. The combined organic layers were dried over anhydrous Na$_2$SO$_4$ and concentrated under reduced pressure to give methyl 10-[6-(tert-butoxycarbonylamino)hexoxy]-6-ethyl-11-methoxy-2-oxo-7,8-dihydro-6H-pyrido[2,1-a][2]benzazepine-3-carboxylate (200 mg), which was used in the next step without further purification.

Step 2: Preparation of 10-[6-(tert-butoxycarbonylamino)hexoxy]-6-ethyl-11-methoxy-2-oxo-7,8-dihydro-6H-pyrido[2,1-a][2]benzazepine-3-carboxylic acid

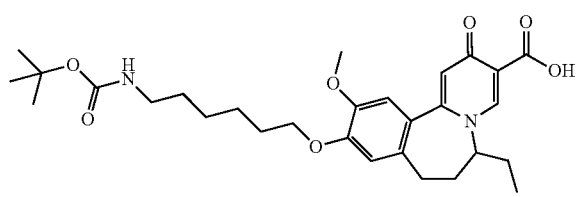 [SMILES: CCC1CCc2cc(OCCCCCCNC(=O)OC(C)(C)C)c(OC)cc2-c2cc(=O)c(C(=O)O)cn21]

A solution of methyl 10-[6-(tert-butoxycarbonylamino)hexoxy]-6-ethyl-11-methoxy-2-oxo-7,8-dihydro-6H-pyrido[2,1-a][2]benzazepine-3-carboxylate (200 mg, 0.37 mmol) and NaOH (29 mg) in MeOH (5 mL) and H$_2$O (0.3 mL) was stirred at 15° C. for 16 hrs. The mixture was acidified with 1 M hydrochloric acid to pH=3-4, and then concentrated under reduced pressure. The residue was purified by prep-HPLC to give 10-[6-(tert-butoxycarbonylamino)hexoxy]-6-ethyl-11-methoxy-2-oxo-7,8-dihydro-6H-pyrido[2,1-a][2]benzazepine-3-carboxylic acid (10 mg) as a white solid. $^1$H NMR (400 MHz, CD$_3$OD) δ ppm 8.73 (s, 1H), 7.16 (s, 1H), 6.95 (s, 1H), 6.85 (s, 1H) 4.08 (t, 2H), 3.90 (s, 3H), 3.05 (t, 2H), 2.71 (d, 1H), 2.26-2.56 (m, 2H), 1.98-2.22 (m, 3H), 1.76-1.91 (m, 3H), 1.48-1.61 (m, 4H), 1.43 (m, 11H), 0.94 (t, 3H). MS obsd. (ESI$^+$) [(M+H)$^+$]: 529.

Example 5: 10-(6-Aminohexoxy)-6-ethyl-11-methoxy-2-oxo-7,8-dihydro-6H-pyrido[2,1-a][2]benzazepine-3-carboxylic acid

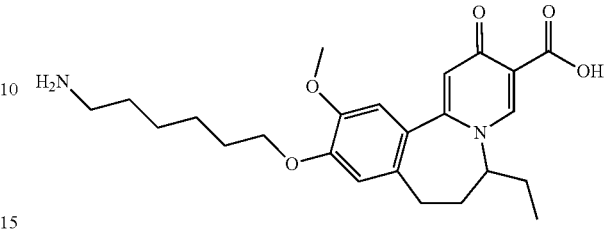

A mixture of 10-[6-(tert-butoxycarbonylamino)hexoxy]-6-ethyl-11-methoxy-2-oxo-7,8-dihydro-6H-pyrido[2,1-a][2]benzazepine-3-carboxylic acid (200 mg, 0.38 mmol) in a solution of HCl in MeOH (2 mL, 4.0 M) was stirred at 15° C. for 16 hrs. The mixture was concentrated under reduced pressure, and the residue was purified by prep-HPLC to give 10-(6-aminohexoxy)-6-ethyl-11-methoxy-2-oxo-7,8-dihydro-6H-pyrido[2,1-a][2]benzazepine-3-carboxylic acid (80 mg) as a yellow solid. $^1$H NMR (400 MHz, CD$_3$OD) δ ppm 8.96 (s, 1H), 7.39 (s, 1H), 7.25 (s, 1H), 7.02 (s, 1H), 4.13 (t, 2H), 3.93 (s, 3H), 2.96 (t, 2H), 2.79 (d, J=6.53 Hz, 1H), 2.48 (m, 2H), 2.10-2.36 (m, 3H), 1.84-1.95 (m, 2H), 1.72 (dt, 2H), 1.44-1.65 (m, 5H), 0.89-1.04 (m, 3H). MS obsd. (ESI$^+$) [(M+H)$^+$]: 429.

Example 6: 10-(6-Acetamidohexoxy)-6-ethyl-11-methoxy-2-oxo-7,8-dihydro-6H-pyrido[2,1-a][2]benzazepine-3-carboxylic acid

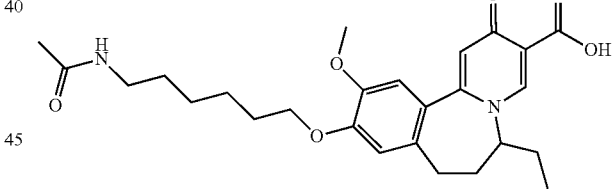

Step 1: Preparation of methyl 10-(6-aminohexoxy)-6-ethyl-11-methoxy-2-oxo-7,8-dihydro-6H-pyrido[2,1-a][2]benzazepine-3-carboxylate hydrochloride

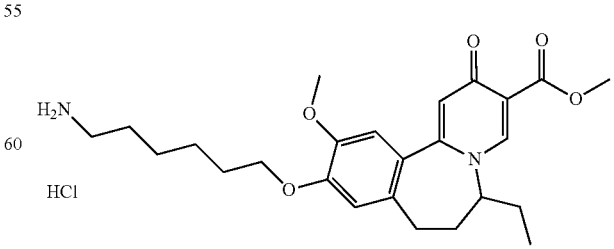

To a stirred solution of compound methyl 10-[6-(tert-butoxycarbonylamino)hexoxy]-6-ethyl-11-methoxy-2-oxo- 7,8-dihydro-6H-pyrido[2,1-a][2]benzazepine-3-carboxylate (700 mg, 1.29 mmol) in MeOH (5 mL) was added a solution of HCl in 1,4-dioxane (self-made, about 4 M, 2 mL) at 15° C. The mixture was stirred at this temperature for 16 hrs, then concentrated under reduced pressure to give crude methyl 10-(6-aminohexoxy)-6-ethyl-11-methoxy-2-oxo-7,8-dihydro-6H-pyrido[2,1-a][2]benzazepine-3-carboxylate hydrochloride (1.0 g) which was used in the next step without further purification.

Step 2: Preparation of methyl 10-(6-acetamidohexoxy)-6-ethyl-11-methoxy-2-oxo-7,8-dihydro-6H-pyrido[2,1-a][2]benzazepine-3-carboxylate

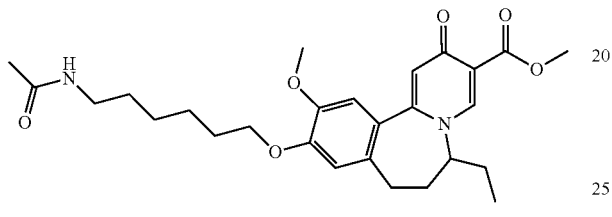

To a stirred solution of methyl 10-(6-aminohexoxy)-6-ethyl-11-methoxy-2-oxo-7,8-dihydro-6H-pyrido[2,1-a][2]benzazepine-3-carboxylate hydrochloride (500 mg, 1.13 mmol) and Et$_3$N (343 mg, 3.39 mmol) in DCM (10 mL) was added acetyl chloride (443 mg, 5.65 mmol) at 0° C. The mixture was stirred at 15° C. for 16 hrs, then the reaction was quenched by addition of H$_2$O (5 mL). The resulting mixture was extracted with DCM (20 mL) for three times. The combined organic layers were washed with 1 M hydrochloric acid (10 mL) twice, saturated NaHCO$_3$ aqueous solution (15 mL) and brine (20 mL) sequentially, then dried over anhydrous Na$_2$SO$_4$ and concentrated under reduced pressure to afford crude methyl 10-(6-acetamidohexoxy)-6-ethyl-11-methoxy-2-oxo-7,8-dihydro-6H-pyrido[2,1-a][2]benzazepine-3-carboxylate (250 mg) as a yellow oil which was used directly in the next step without further purification.

Step 3: Preparation of 10-(6-acetamidohexoxy)-6-ethyl-11-methoxy-2-oxo-7,8-dihydro-6H-pyrido[2,1-a][2]benzazepine-3-carboxylic acid

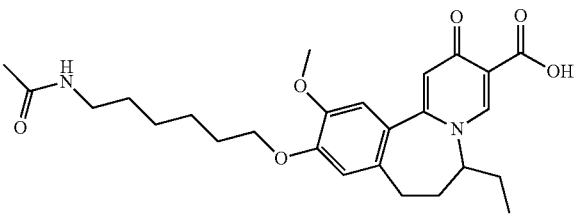 [SMILES: CCC1CCc2cc(OCCCCCCNC(C)=O)c(OC)cc2-c2cc(=O)c(C(=O)O)cn21]

A solution of methyl 10-(6-acetamidohexoxy)-6-ethyl-11-methoxy-2-oxo-7,8-dihydro-6H-pyrido[2,1-a][2]benzazepine-3-carboxylate (250 mg, 0.52 mmol) and NaOH (62 mg) in MeOH (5 mL) and H$_2$O (0.8 mL) was stirred at 15° C. for 4 hrs. Then the mixture was acidified to pH=3-4 with 1 M hydrochloric acid, and then concentrated under reduced pressure. The residue was purified by prep-HPLC to give 10-(6-acetamidohexoxy)-6-ethyl-11-methoxy-2-oxo-7,8-dihydro-6H-pyrido[2,1-a][2]benzazepine-3-carboxylic acid (9 mg) as a white solid. $^1$H NMR (400 MHz, CD$_3$OD) δ ppm 8.70 (s, 1H), 7.08 (s, 1H), 6.90 (s, 1H), 6.54-6.75 (m, 1H), 4.06 (m., 2H), 3.86 (s, 3H), 3.15-3.20 (m, 2H), 2.68 (m, 1H), 2.22-2.50 (m, 2H), 2.00-2.13 (m, 2H), 1.93 (s, 3H), 1.82 (d, 2H), 1.35-1.60 (m, 8H), 0.90 (m, 3H). MS obsd. (ESI$^+$) [(M+H)$^+$]: 471.

Example 7: 6-Ethyl-10-[6-(methanesulfonamido)hexoxy]-11-methoxy-2-oxo-7,8-dihydro-6H-pyrido[2,1-a][2]benzazepine-3-carboxylic acid

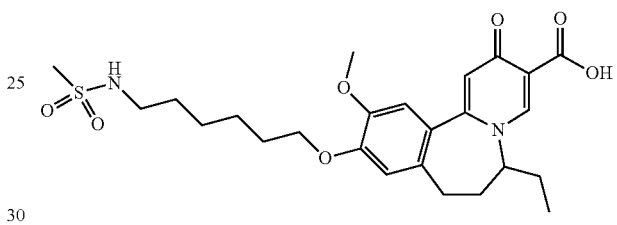

Step 1: Preparation of methyl 6-ethyl-10-[6-(methanesulfonamido)hexoxy]-11-methoxy-2-oxo-7,8-dihydro-6H-pyrido[2,1-a][2]benzazepine-3-carboxylate

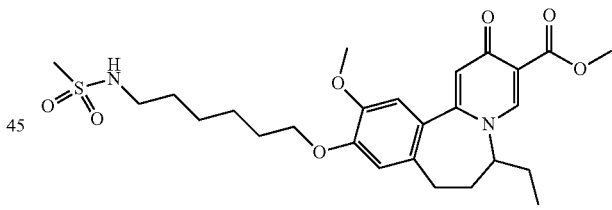

To a stirred solution of compound methyl 10-(6-aminohexoxy)-6-ethyl-11-methoxy-2-oxo-7,8-dihydro-6H-pyrido[2,1-a][2]benzazepine-3-carboxylate hydrochloride (500 mg, 1.13 mmol) and triethylamine (343 mg, 3.39 mmol) in DCM (10 mL) was added methanesulfonyl chloride (720 mg, 6.29 mmol) at 0° C. The mixture was stirred at 0° C. for 1 hr, and then diluted with H$_2$O (5 mL). The resulting mixture was extracted with DCM (20 mL) for three times. The combined organic layers were washed sequentially with 1 M hydrochloric acid, saturated NaHCO$_3$ aqueous solution (15 mL) and brine (20 mL), then dried over anhydrous Na$_2$SO$_4$ and concentrated under reduced pressure to afford crude methyl 6-ethyl-10-[6-(methanesulfonamido)hexoxy]-11-methoxy-2-oxo-7,8-dihydro-6H-pyrido[2,1-a][2]benzazepine-3-carboxylate (500 mg) as a yellow oil, which was used directly in the next step without further purification.

Step 2: Preparation of 6-ethyl-10-[6-(methanesulfonamido)hexoxy]-11-methoxy-2-oxo-7,8-dihydro-6H-pyrido[2,1-a][2]benzazepine-3-carboxylic acid

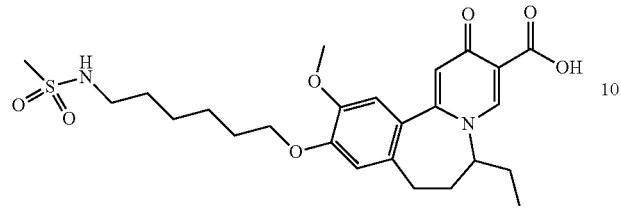

A solution of methyl 6-ethyl-10-[6-(methanesulfonamido)hexoxy]-11-methoxy-2-oxo-7,8-dihydro-6H-pyrido[2,1-a][2]benzazepine-3-carboxylate (500 mg, 0.96 mmol) and NaOH (115 mg) in MeOH (5 mL) and H$_2$O (1 mL) was stirred at 15° C. for 4 hrs. The mixture was acidified with 1 M hydrochloric acid to pH=3-4, and then concentrated under reduced pressure. The residue was purified by prep-HPLC to give 6-ethyl-10-[6-(methanesulfonamido)hexoxy]-11-methoxy-2-oxo-7,8-dihydro-6H-pyrido[2,1-a][2]benzazepine-3-carboxylic acid (13 mg) as a white solid. $^1$H NMR (400 MHz, CD$_3$OD) δ ppm 8.70 (s, 1H), 7.11 (s, 1H), 6.49-6.99 (m, 2H), 4.09 (t, 2H), 3.88 (s, 3H), 3.07 (t, 2H), 2.92 (s, 3H), 2.70 (m, 1H), 2.23-2.54 (m, 2H), 1.97-2.18 (m, 2H), 1.80-1.90 (m, 2H), 1.42-1.67 (m, 8H), 0.92 (m, 3H). MS obsd. (ESI$^+$)[(M+H)$^+$]: 507.

Example 8: 6-Ethyl-11-methoxy-10-(3-methylsulfanylpropoxy)-2-oxo-7,8-dihydro-6H-pyrido[2,1-a][2]benzazepine-3-carboxylic acid

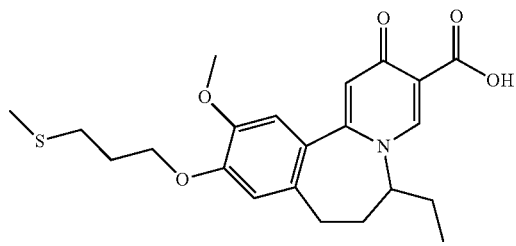 [SMILES: CCC1CCc2cc(OCCCSC)c(OC)cc2-c2cc(=O)c(C(=O)O)cn21]

Step 1: Preparation of 3-methylsulfanylpropyl methanesulfonate

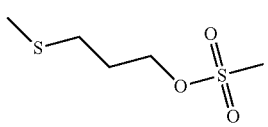

To a stirred solution of 3-methylsulfanylpropan-1-ol (500 mg, 4.71 mmol) and triethylamine (715 mg, 7.06 mmol) in DCM (20 mL) was added methanesulfonyl chloride (900 mg, 7.86 mmol) at 0° C. The mixture was stirred at 0° C. for 1 hr. The mixture was partitioned between H$_2$O and DCM. The organic layer was washed with 1 M hydrochloric acid and brine, dried over anhydrous Na$_2$SO$_4$, and concentrated under reduced pressure to give 3-methylsulfanylpropyl methanesulfonate (750 mg) as yellow oil.

Step 2: Preparation of methyl 6-ethyl-11-methoxy-10-(3-methylsulfanylpropoxy)-2-oxo-7,8-dihydro-6H-pyrido[2,1-a][2]benzazepine-3-carboxylate

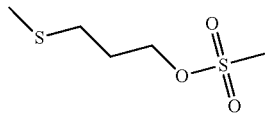

A mixture of methyl 6-ethyl-10-hydroxy-11-methoxy-2-oxo-7,8-dihydro-6H-pyrido[2,1-a][2]benzazepine-3-carboxylate (100 mg, 0.29 mmol), 3-methylsulfanylpropyl methanesulfonate (64 mg, 0.35 mmol) and K$_2$CO$_3$ (60 mg, 0.44 mmol) in DMF (3 mL) was heated at 60° C. with stirring for 4 hrs. After being cooled to rt, the mixture was diluted with H$_2$O (10 mL). The resulting mixture was extracted with EtOAc (20 mL) for three times. The combined organic layers were dried over anhydrous Na$_2$SO$_4$ and concentrated under reduced pressure to give crude methyl 6-ethyl-11-methoxy-10-(3-methylsulfanylpropoxy)-2-oxo-7,8-dihydro-6H-pyrido[2,1-a][2]benzazepine-3-carboxylate (200 mg) as yellow oil, which was used directly in the next step without further purification.

Step 3: Preparation of 6-ethyl-11-methoxy-10-(3-methylsulfanylpropoxy)-2-oxo-7,8-dihydro-6H-pyrido[2,1-a][2]benzazepine-3-carboxylic acid

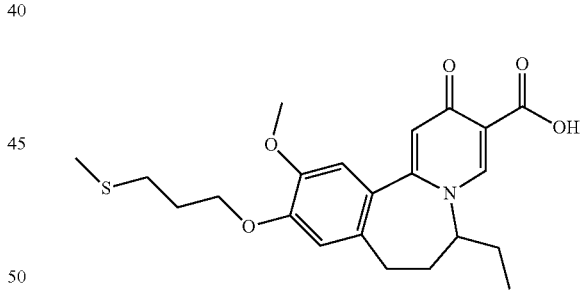

A solution of crude methyl 6-ethyl-11-methoxy-10-(3-methylsulfanylpropoxy)-2-oxo-7,8-dihydro-6H-pyrido[2,1-a][2]benzazepine-3-carboxylate (200 mg, 0.46 mmol) and NaOH (37 mg) in MeOH (2 mL) and H$_2$O (0.5 mL) was stirred at 15° C. for 12 hrs. The mixture was acidified with 1M hydrochloric acid to pH=3-4, and then concentrated under reduced pressure. The residue was purified by prep-HPLC to give 6-ethyl-11-methoxy-10-(3-methylsulfanylpropoxy)-2-oxo-7,8-dihydro-6H-pyrido[2,1-a][2]benzazepine-3-carboxylic acid (10 mg) as a white solid, $^1$H NMR (400 MHz, CD$_3$OD) δ ppm 8.73 (s, 1H), 7.18 (s, 1H), 6.98 (s, 1H), 6.88 (s, 1H), 4.19 (t, 2H), 3.91 (s, 3H), 2.65-2.79 (m, 4H), 2.43-2.56 (m, 1H), 2.13-2.40 (m, 2H), 2.08-2.13 (m, 7H). MS obsd. (ESI$^+$) [(M+H)$^+$]: 418.

Example 9: 6-Ethyl-11-methoxy-10-(3-methylsulfonylpropoxy)-2-oxo-7,8-dihydro-6H-pyrido[2,1-a][2]benzazepine-3-carboxylic acid

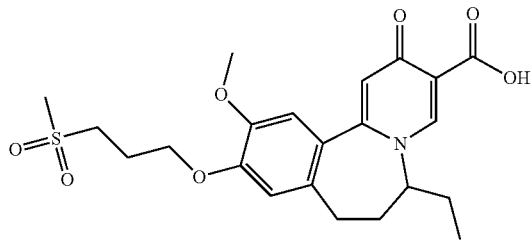 [SMILES: CCC1CCc2cc(OCCCS(C)(=O)=O)c(OC)cc2-c2cc(=O)c(C(=O)O)cn21]

Step 1: Preparation of 3-methylsulfonylpropyl 4-methylbenzenesulfonate

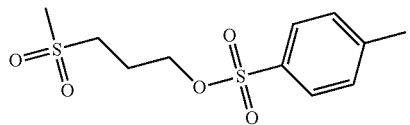 [SMILES: Cc1ccc(S(=O)(=O)OCCCS(C)(=O)=O)cc1]

To a stirred solution of 3-methylsulfonylpropan-1-ol (500 mg, 3.62 mmol) in DCM (10 mL) was added triethylamine (549 mg, 5.43 mmol). Then to the mixture was added a solution of tosyl chloride (759 mg, 3.98 mmol) in DCM (10 mL) at 0° C. The resulting mixture was stirred at 15° C. for 12 hrs, and then partitioned between DCM and H$_2$O. The separated organic layer was washed sequentially with water, hydrochloric acid and brine, then dried over anhydrous Na$_2$SO$_4$ and concentrated under reduced pressure give 3-methylsulfonylpropyl 4-methylbenzenesulfonate (900 mg) as a light yellow oil, which was used directly in the next step without further purification.

Step 2: Preparation of methyl 6-ethyl-11-methoxy-10-(3-methylsulfonylpropoxy)-2-oxo-7,8-dihydro-6H-pyrido[2,1-a][2]benzazepine-3-carboxylate

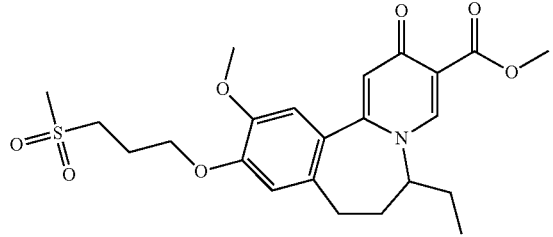 [SMILES: CCC1CCc2cc(OCCCS(C)(=O)=O)c(OC)cc2-c2cc(=O)c(C(=O)OC)cn21]

A mixture of methyl 6-ethyl-10-hydroxy-11-methoxy-2-oxo-7,8-dihydro-6H-pyrido[2,1-a][2]benzazepine-3-carboxylate (100 mg, 0.29 mmol), 3-methylsulfonylpropyl 4-methylbenzenesulfonate (102 mg, 0.35 mmol) and K$_2$CO$_3$ (60 mg, 0.44 mmol) in DMF (3 mL) was heated at 60° C. with stirring for 4 hrs. After being cooled to rt, the mixture was diluted with H$_2$O (10 mL), and extracted with EtOAc (20 mL) for three times. The combined organic layers were dried over anhydrous Na$_2$SO$_4$ and concentrated under reduced pressure to give crude methyl 6-ethyl-11-methoxy-10-(3-methylsulfonylpropoxy)-2-oxo-7,8-dihydro-6H-pyrido[2,1-a][2]benzazepine-3-carboxylate (240 mg) as a yellow oil, which was used directly in the next step without purification.

Step 3: Preparation of 6-ethyl-11-methoxy-10-(3-methylsulfonylpropoxy)-2-oxo-7,8-dihydro-6H-pyrido[2,1-a][2]benzazepine-3-carboxylic acid

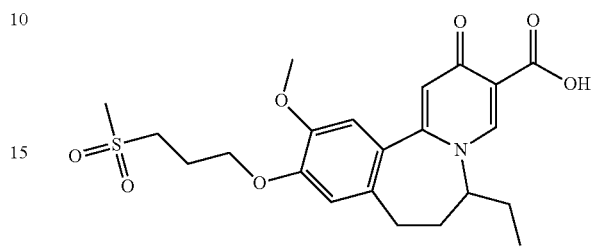

A solution of crude methyl 6-ethyl-11-methoxy-10-(3-methylsulfonylpropoxy)-2-oxo-7,8-dihydro-6H-pyrido[2,1-a][2]benzazepine-3-carboxylate (240 mg, 0.52 mmol) and NaOH (41 mg) in MeOH (3 mL) and H$_2$O (0.5 mL) was stirred at 15° C. for 12 hrs. The mixture was acidified with 1 M hydrochloric acid to pH=3-4, and then concentrated under reduced pressure. The residue was purified by prep-HPLC to give 6-ethyl-11-methoxy-10-(3-methylsulfonylpropoxy)-2-oxo-7,8-dihydro-6H-pyrido[2,1-a][2]benzazepine-3-carboxylic acid (10 mg) as a white solid. $^1$H NMR (400 MHz, CD$_3$OD) δ ppm 8.73 (s, 1H), 7.19 (s, 1H), 6.99 (s, 1H), 6.87 (s, 1H), 4.24 (t, 2H), 3.92 (s, 3H), 3.34-3.40 (m, 2H), 3.03 (s, 3H), 2.66-2.80 (m, 2H), 2.50 (d, 1H), 2.28-2.38 (m, 3H), 1.98-2.22 (m, 3H), 0.94 (t, 3H). MS obsd. (ESI$^+$) [(M+H)$^{+}$]: 450.

Example 10: 6-Ethyl-11-methoxy-2-oxo-10-(2,2,2-trifluoroethoxy)-7,8-dihydro-6H-pyrido[2,1-a][2]benzazepine-3-carboxylic acid

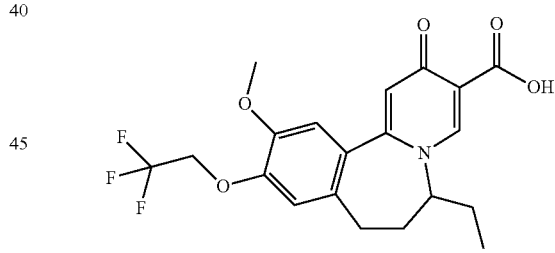

Step 1: Preparation of methyl 6-ethyl-11-methoxy-2-oxo-10-(2,2,2-trifluoroethoxy)-7,8-dihydro-6H-pyrido[2,1-a][2]benzazepine-3-carboxylate

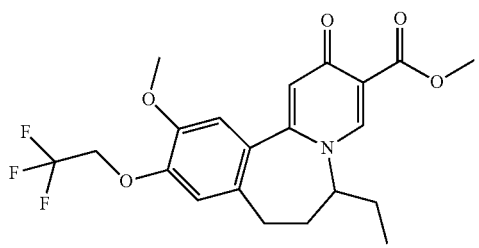 [SMILES: CCC1CCc2cc(OCC(F)(F)F)c(OC)cc2-c2cc(=O)c(C(=O)OC)cn21]

A mixture of methyl 6-ethyl-10-hydroxy-11-methoxy-2-oxo-7,8-dihydro-6H-pyrido[2,1-a][2]benzazepine-3-carboxylate (100 mg, 0.29 mmol), 1,1,1-trifluoro-2-iodo-ethane (92 mg, 0.44 mmol) and $K_2CO_3$ (81 mg, 0.58 mmol) in DMF (3 mL) was heated at 90° C. with stirring for 12 hrs. After being cooled to rt, the mixture was diluted with $H_2O$ (10 mL), and extracted with EtOAc (20 mL) for three times. The combined organic layers were dried over anhydrous $Na_2SO_4$ and concentrated under reduced pressure to give crude methyl 6-ethyl-11-methoxy-2-oxo-10-(2,2,2-trifluoroethoxy)-7,8-dihydro-6H-pyrido[2,1-a][2]benzazepine-3-carboxylate (250 mg) as a yellow oil, which was used directly in the next step without further purification.

Step 2: Preparation of 6-ethyl-11-methoxy-2-oxo-10-(2,2,2-trifluoroethoxy)-7,8-dihydro-6H-pyrido[2,1-a][2]benzazepine-3-carboxylic acid

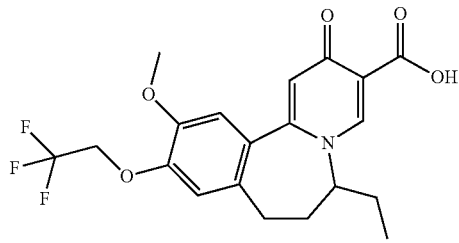 [SMILES: CCC1CCc2cc(OCC(F)(F)F)c(OC)cc2-c2cc(=O)c(C(=O)O)cn21]

A solution of methyl 6-ethyl-11-methoxy-2-oxo-10-(2,2,2-trifluoroethoxy)-7,8-dihydro-6H-pyrido[2,1-a][2]benzazepine-3-carboxylate (250 mg, 0.59 mmol) and NaOH (59 mg/0.7 mL) in MeOH (3 mL) and $H_2O$ (0.7 mL) was stirred at 15° C. for 12 hrs. The resulting mixture was acidified with 1 M hydrochloric acid to pH=3-4, and then concentrated under reduced pressure. The residue was purified by recrystallization from $CH_3CN/H_2O$ to give 6-ethyl-11-methoxy-2-oxo-10-(2,2,2-trifluoroethoxy)-7,8-dihydro-6H-pyrido[2,1-a][2]benzazepine-3-carboxylic acid (8 mg) as a white solid, $^1H$ NMR (400 MHz, DMSO-d6) δ ppm 8.60 (s, 1H), 7.20 (s, 1H), 7.11 (s, 2H), 6.55 (s, 1H), 4.78 (q, 2H), 3.86 (s, 3H), 2.57-2.75 (m, 2H), 2.32 (m, 1H), 1.86-2.21 (m, 4H), 0.83 (m, 3H). MS obsd. (ESI+) [(M+H)+]: 412.

BIOLOGICAL EXAMPLES

Example 11 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 µL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation, Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their capacity to inhibit HBsAg as described herein. The Examples were tested in the above assay and found to have $IC_{50}$ of about 0.001 µM to about 50.0 µM. Particular compounds of formula I were found to have $IC_{50}$ of about 0.001 µM to about 1.0 µM. Results of HBsAg assay are given in Table 1.

TABLE 1

Activity data of particular compounds

| Example No. | $IC_{50}$ (µM) |
| --- | --- |
| 1 | 35.394 |
| 2 | 1.076 |
| 3 | 0.419 |
| 4 | 0.619 |
| 5 | 0.602 |
| 6 | 12.384 |
| 7 | 5.866 |
| 8 | 1.892 |
| 9 | 1.068 |
| 10 | 0.558 |

We claim:
1. A compound of formula (I),

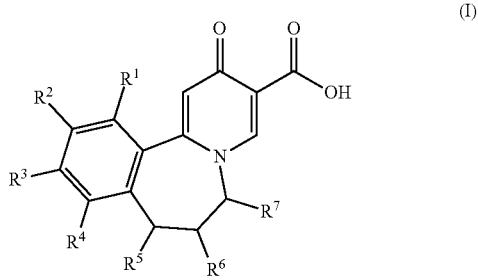

wherein:
$R^1$, $R^2$, $R^3$ and $R^4$ are independently selected from $C_{1-6}$alkyl, halo$C_{1-6}$alkyl, hydrogen, halogen, amino, cyano, pyrrolidinyl and $OR^8$;
$R^5$, $R^6$, $R^7$ are independently selected from hydrogen, $C_{1-6}$alkyl or halo$C_{1-6}$alkyl;
$R^8$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$alkyl;

$C_{1-6}$alkoxy$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkoxycarbonylamino$C_{1-6}$alkyl; pyrazolyl$C_{1-6}$alkyl or triazolyl$C_{1-6}$alkyl;

or a pharmaceutically acceptable salt, or an enantiomer, or diastereomer thereof.

2. The compound of formula I according to claim 1, wherein $R^1$ is hydrogen;
$R^2$ is $C_{1-6}$alkoxy;
$R^3$ is OR, wherein $R^8$ is selected from $C_{1-6}$alkyl, halo-$C_{1-6}$alkyl, phenyl$C_{1-6}$alky, $C_{1-6}$alkoxy$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl and $C_{1-6}$alkoxycarbonylamino$C_{1-6}$alkyl;
$R^4$ is hydrogen;
$R^5$ is hydrogen;
$R^6$ is hydrogen;
$R^7$ is hydrogen or $C_{1-6}$alkyl;

or a pharmaceutically acceptable salt, or an enantiomer, or diastereomer thereof.

3. The compound of formula I according to claim 2, wherein $R^1$ is hydrogen;
$R^2$ is methoxy;
$R^3$ is methoxy, trifluoroethoxy, benzyloxy, methoxypropoxy, methylsulfanylpropoxy, methylsulfonylpropoxy, aminohexyloxy, methylcarbonylaminohexyloxy, methylsulfonylaminohexyloxy or tert-butoxycarbonylaminohexyloxy;
$R^4$ is hydrogen;
$R^5$ is hydrogen;
$R^6$ is hydrogen;
$R^7$ is hydrogen or ethyl;

or a pharmaceutically acceptable salt, or an enantiomer, or diastereomer thereof.

4. The compound according to claim 1, or a pharmaceutically acceptable salt, or an enantiomer, or diastereomer thereof, wherein $R^1$ is hydrogen; $R^2$ is $C_{1-6}$alkoxy; $R^4$ is hydrogen; $R^5$ is hydrogen; $R^6$ is hydrogen.

5. The compound according to claim 1, or a pharmaceutically acceptable salt, or an enantiomer, or diastereomer thereof, wherein $R^1$ is hydrogen; $R^2$ is methoxy; $R^4$ is hydrogen; $R^5$ is hydrogen; $R^6$ is hydrogen.

6. The compound according to claim 1, or a pharmaceutically acceptable salt, or an enantiomer, or diastereomer thereof, wherein $R^3$ is OR, wherein $R^8$ is $C_{1-6}$alkoxy-$C_{1-6}$alkyl, $C_{1-6}$alkylsulfanyl$C_{1-6}$alkyl, $C_{1-6}$alkylsulfonylamino$C_{1-6}$alkyl or $C_{1-6}$alkoxycarbonylamino$C_{1-6}$alkyl.

7. The compound according to claim 1, or a pharmaceutically acceptable salt, or an enantiomer, or diastereomer thereof, wherein $R^3$ is methoxypropoxy, methylsulfanylpropoxy, methylsulfonylaminohexyloxy or tert-butoxycarbonylaminohexyloxy.

8. The compound according to claim 1, or a pharmaceutically acceptable salt, or an enantiomer, or diastereomer thereof, wherein $R^7$ is $C_{1-6}$alkyl.

9. The compound according to claim 8, or a pharmaceutically acceptable salt, or an enantiomer, or diastereomer thereof, wherein $R^7$ is ethyl.

10. The compound according to claim 1, which compound is selected from the group consisting of:
- 10,11-Dimethoxy-2-oxo-7,8-dihydro-6H-pyrido[2,1-a][2]benzazepine-3-carboxylic acid;
- 10-Benzyloxy-6-ethyl-11-methoxy-2-oxo-7,8-dihydro-6H-pyrido[2,1-a][2]benzazepine-3-carboxylic acid;
- 6-Ethyl-11-methoxy-10-(3-methoxypropoxy)-2-oxo-7,8-dihydro-6H-pyrido[2,1-a][2]benzazepine-3-carboxylic acid;
- 10-[6-(Tert-butoxycarbonylamino)hexoxy]-6-ethyl-11-methoxy-2-oxo-7,8-dihydro-6H-pyrido[2,1-a][2]benzazepine-3-carboxylic acid;
- 10-(6-Aminohexoxy)-6-ethyl-11-methoxy-2-oxo-7,8-dihydro-6H-pyrido[2,1-a][2]benzazepine-3-carboxylic acid;
- 10-(6-Acetamidohexoxy)-6-ethyl-11-methoxy-2-oxo-7,8-dihydro-6H-pyrido[2,1-a][2]benzazepine-3-carboxylic acid;
- 6-Ethyl-10-[6-(methanesulfonamido)hexoxy]-11-methoxy-2-oxo-7,8-dihydro-6H-pyrido[2,1-a][2]benzazepine-3-carboxylic acid;
- 6-Ethyl-11-methoxy-10-(3-methylsulfanylpropoxy)-2-oxo-7,8-dihydro-6H-pyrido[2,1-a][2]benzazepine-3-carboxylic acid;
- 6-Ethyl-11-methoxy-10-(3-methylsulfonylpropoxy)-2-oxo-7,8-dihydro-6H-pyrido[2,1-a][2]benzazepine-3-carboxylic acid; and,
- 6-Ethyl-11-methoxy-2-oxo-10-(2,2,2-trifluoroethoxy)-7,8-dihydro-6H-pyrido[2,1-a][2]benzazepine-3-carboxylic acid;

or a pharmaceutically acceptable salt, or an enantiomer, or diastereomer thereof.

11. The compound according to claim 10, which compound is selected from the group consisting of
- 6-Ethyl-11-methoxy-10-(3-methoxypropoxy)-2-oxo-7,8-dihydro-6H-pyrido[2,1-a][2]benzazepine-3-carboxylic acid;
- 6-Ethyl-10-[6-(methanesulfonamido)hexoxy]-11-methoxy-2-oxo-7,8-dihydro-6H-pyrido[2,1-a][2]benzazepine-3-carboxylic acid; and,
- 6-Ethyl-11-methoxy-2-oxo-10-(2,2,2-trifluoroethoxy)-7,8-dihydro-6H-pyrido[2,1-a][2]benzazepine-3-carboxylic acid;

or a pharmaceutically acceptable salt, or an enantiomer, or diastereomers thereof.

12. A pharmaceutical composition comprising a compound in accordance with claim 1 and a at least one therapeutically acceptable carrier, diluent or excipient.

* * * * *